United States Patent [19]

Woolard

[11] Patent Number: 4,877,880

[45] Date of Patent: Oct. 31, 1989

[54] PROCESS FOR PREPARATION OF IMINOTHIAZOLIDINES

[75] Inventor: Frank X. Woolard, Richmond, Calif.

[73] Assignee: ICI Americas Inc., Wilmington, Del.

[21] Appl. No.: 282,807

[22] Filed: Dec. 9, 1988

Related U.S. Application Data

[63] Continuation-in-part of Ser. No. 126,134, Nov. 17, 1987, abandoned.

[51] Int. Cl.$^4$ ............................................. C07D 277/18
[52] U.S. Cl. ....................................... 548/190; 564/29
[58] Field of Search ........................................... 548/190

[56] References Cited

U.S. PATENT DOCUMENTS 3,804,848  4/1974  Behner .................................. 548/190
4,326,876  4/1982  Aoyagi .................................. 548/190

OTHER PUBLICATIONS

Dains et al., JACS, vol. 44, pp. 2637-2643.
Cholpankulova et al., Izv. Akad. Nauk Kaz. SSR, Ser. Khim., 1984 (6), pp. 75-81.

Primary Examiner—Robert Gerstl
Attorney, Agent, or Firm—Joel G. Ackerman; Paul R. Martin

[57] ABSTRACT

A process for the preparation of certain iminothiazolidines of the formula

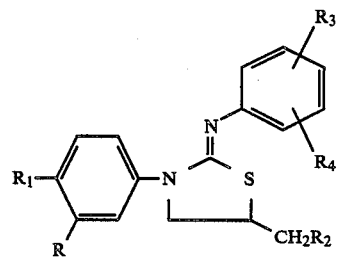

in which R is halo, nitro, cyano, $C_1$-$C_4$ alkyl, $C_1$-$C_4$ alkoxy, pentahalomethyl, difluoromethyl, pentafluoroethyl, trifluoromethylthio, difluoromethoxy, trifluoromethoxy, tetrafluoroethoxy, methylsulfonyl, $C_1$-$C_4$ alkyloxyiminomethyl, benzyloxyiminomethyl, 1-($C_1$-$C_4$)alkyl oxyiminoethyl or 1-benzyloxyiminoethyl; $R_1$ is hydrogen or halo; $R_2$ is hydrogen, $C_1$-$C_4$ alkyl or $C_1$-$C_4$ haloalkyl; and $R_3$ and $R_4$ are independently hydrogen, halo, nitro, cyano, $C_1$-$C_4$ alkyl, $C_1$-$C_4$ haloalkyl, $C_1$-$C_4$alkoxy, $C_1$-$C_4$ fluoroalkoxy or $C_1$-$C_4$ alkylthio, by reacting a thiourea with methanesulfonic acid or trifluoromethanesulfonic acid in an aprotic solvent for a period of time and at a temperature sufficient to achieve cyclization of the thiourea to form said iminothiazolidine.

The thiourea may be prepared by reaction of an N-3-substituted allyl aniline with an arylisothiocyanate.

10 Claims, No Drawings

PROCESS FOR PREPARATION OF IMINOTHIAZOLIDINES

CROSS REFERENCE TO RELATED APPLICATIONS

This is a continuation-in-part of application Ser. No. 126,134, filed Nov. 17, 1987 now abandoned.

The present invention relates to a process for the preparation of certain iminothiazolidines, compounds which have been found to be effective as herbicidal agents.

BACKGROUND OF THE INVENTION

The thiazolidine compounds which may be produced by the process of the invention described herein have the formula

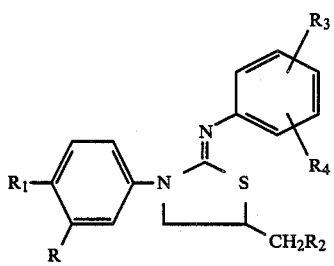

in which

R is halo, nitro, cyano, $C_1$-$C_4$ alkyl, $C_1$-$C_4$ alkoxy, pentahalomethyl, difluoromethyl, pentafluoroethyl, trifluoromethylthio, difluoromethoxy, trifluoromethoxy, tetrafluoroethoxy, methylsulfonyl, $C_1$-$C_4$ alkyloxyiminomethyl, benzyloxyiminomethyl, 1-($C_1$-$C_4$ alkyl)oxyiminoethyl or 1-benzyloxyiminoethyl;

$R_1$ is hydrogen or halo;

$R_2$ is hydrogen, $C_1$-$C_4$ alkyl or $C_1$-$C_4$ haloalkyl; and $R_3$ and $R_4$ are independently hydrogen, halo, nitro, cyano, $C_1$-$C_4$ alkyl, $C_1$-$C_4$ haloalkyl, $C_1$-$C_4$ alkoxy, $C_1$-$C_4$ fluoroalkoxy or $C_1$-$C_4$ alkylthio. These compounds are herbicidally active.

DESCRIPTION OF THE INVENTION

The process of the invention comprises reacting a thiourea of the formula

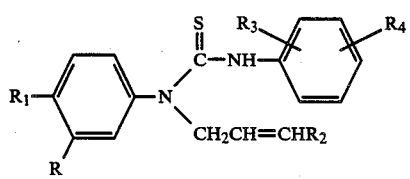

wherein R-$R_1$ are as previously defined, with about one equivalent of methanesulfonic acid or trifluoromethanesulfonic acid in the presence of a suitable aprotic solvent, and continuing said reaction at a temperature and for a sufficient period of time to produce the iminothiazolidine set forth in the formula above. Preferably $R_2$ is alkyl or haloalkyl.

In the process of the invention, the methanesulfonic acid or trifluoromethanesulfonic acid is used to effect cyclization of the thiourea to form the iminothiazolidine.

Practically any inert aprotic solvent, such as halocarbon or hydrocarbon solvents, can be used, for instance, ethylene dichloride, 1,2-dichloroethane, methylene chloride, benzene or toluene. Most preferred is ethylene dichloride.

This reaction may be conducted at temperatures of from about 20° C. to about 45° C., preferably from about 20° C. to about 30° C.

The reaction is also conducted at atmospheric pressure, and for a time sufficient to complete the reaction, which will vary in accordance with the starting materials used. The time will vary from about one to about forty-eight hours, depending upon the specific reactants used, the temperature at which the reaction is conducted, and the like.

The thiourea starting compounds in the process of this invention can be made by reacting an arylisothiocyanate of the formula

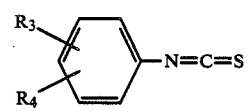

wherein $R_3$ and $R_4$ are the same or different, with an N-3-substituted allyl aniline having the formula

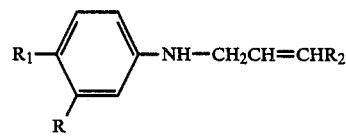

where R-$R_2$ are as previously indicated, in the presence of an organic solvent therefor, and a suitable catalyst, at a temperature and for a sufficient period of time to yield an N,N'-diaryl-N-3-substituted allyl thiourea of the formula

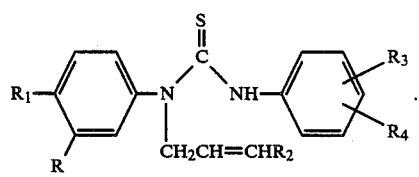

It should be understood that while the core of the process of this invention lies in the reaction of the thiourea compound described above with either methanesulfonic acid or trifluoromethanesulfonic acid dissolved in a solvent system, the invention, in a broader sense, includes the step taken to prepare the thiourea compound itself, namely reacting the aryl isocyanate with the alkenyl aniline compound described above.

The entire reaction can be represented in accordance with the following generalized sequence:

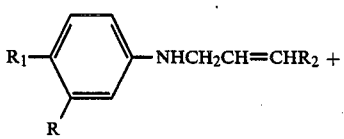

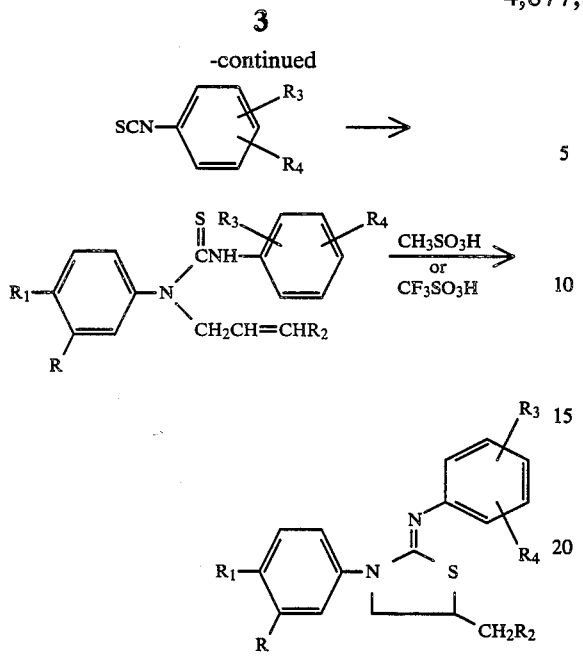

wherein R, R₁, R₂, R₃ and R₄ are as defined.

In one embodiment, R is halo, cyano, trifluoromethyl or trifluoromethylthio and R₁ is hydrogen.

The iminothiazolidines produced in accordance with the method of this invention have herbicidal activity and are described in application Ser. No. 269,819, filed Nov. 15, 1988.

Thiourea compounds formed as intermediates in the process of this invention also have herbicidal activity, and are described and claimed in application Ser. No. 128,005, filed Nov. 30, 1987.

The process of this invention will be more fully understood by reference to the following examples, which are intended to be illustrative of the invention and not limiting thereof. Example 1 illustrates the preparation of the aniline starting compounds, and is not part of the process of the invention.

EXAMPLE 1

Preparation of N-Crotyl-m-trifluoromethyl aniline

To a one-liter, 3-necked round-bottomed flask equipped with a mechanical stirrer, pressure equalizing addition funnel and reflux condenser carrying a nitrogen bubbler was added 5.23 g (0.22 mole) of sodium hydride and 100 mL of tetrahydrofuran. The mixture was stirred and 54.41 g (0.20 mole) of m-trifluoromethyl dichloroacetanilide in 150 mL of tetrahydrofuran was added dropwise over a period of 0.5 hour. When the addition was complete, the stirring was continued until hydrogen evolution was completed (about 0.5 hour). At that time, 22.64 mL of crotyl bromide (0.22 mole) dissolved in 75 mL of tetrahydrofuran were then added dropwise with stirring over a period of 0.5 hour. When this addition was complete, the stirring was continued at room temperature for a period of approximately 16 hours. Thereafter, 10 mL of 3% hydrogen chloride was cautiously added and stirred for 15 minutes. The solution was stripped of its solvent in vacuo and the residue partitioned between 300 mL ethyl acetate and 200 mL of water. The organic phase then washed with 200 mL of water, followed by 200 mL of saturated sodium chloride. The organic phase was dried over sodium sulfate and the solvent removed in vacuo to give 64.64 g (99%) of crude product having an amber-orange color, which was identified as N-crotyl-m-trifluoromethyl dichloroacetanilide.

64.64 grams (g) (0.198 mole) of N-crotyl-m-trifluoromethyl dichloroacetanilide and 300 milliliters (mL) of absolute ethanol were added to a round-bottomed flask, and stirred at room temperature, followed by the addition of 14.39 g of potassium hydroxide in 20 mL of water dropwise over a period of 10 minutes. After the addition was complete, the reaction mixture solidified with the precipitation of potassium dichloroacetate. The flask was swirled by hand to break up the solidified cake and stirring allowed to continue for an additional 18 hours. At the end of this time, 250 mL of ethylacetate was added and the mixture filtered. The solvent was then removed in vacuo to yield a pale orange-yellow semisolid. This was partitioned between 300 mL of ethylacetate and 300 mL of water and the layers were separated. The organic layer was washed one time with 200 mL of water and one time with 200 mL of a saturated sodium chloride solution. The organic layer was then dried with sodium sulfate and the solvent removed in vacuo to yield a yellow-orange material that was distilled at aspirator pressure to yield 36.6 g (86%) of product, N-crotyl-m-trifluoromethyl aniline.

EXAMPLE 2

Preparation of 2-[4-Chloro-2-methyl)phenyl]imino-3-(3-trifluoromethyl)-phenyl-5-ethylthiazolidine N-crotyl-m-trifluoromethyl aniline (7.10 g) was combined with 6.06 g of 4-chloro-2-methylphenylisothiocyanate in 20 mL of acetonitrile and approximately 100 mg of a catalyst, 1,4-diazobicyclo[2.2.2]-octane. The reaction mixture was stirred for 6.5 hours.

The stirring was continued overnight and the next morning 50 mL of ethylacetate was added. The solution was then washed 3 times with 25 mL of 3% hydrochloric acid. The organic phase was dried with sodium sulfate and the solvent removed in vacuo to yield 13.0 g (99%) of product. This was identified as N-crotyl-N-(3-trifluoromethyl)phenyl-N'-(4-chloro-2-methyl)phenyl-thiourea.

Next, 11.05 g of N-crotyl-N-(3-trifluoromethyl)phenyl-N'-(4-chloro-2-methyl)phenyl thiourea, 4.16 g trifluoromethane sulfonic acid and 100 mL 1,2-dichloroethane were combined and stirred for 0.5 hour and continued for 64 hours.

Following this, the solution was washed 3 times with 50 mL of saturated potassium carbonate solution and dried over sodium sulfate. The solvent was removed in vacuo, and the residual oil chromatographed on silica gel (30% ethyl acetate/70% hexane) to yield 5.27 g (48%) of product.

EXAMPLE 3

Preparation of 2-(3-trifluoromethyl)phenylimino-3-(3-trifluoromethyl)-phenyl-5-ethylthiazolidine A quantity of N-crotyl-N-(3-trifluoromethyl)phenyl-N'-(3-trifluoromethyl)phenylthiourea was prepared in accordance with the same general techniques set forth in Examples 1 and 2, except that 3-trifluoromethylphenyl isothiocyanate was used instead of 4-chloro-2-methylphenyl isothiocyanate. After the thiourea was prepared, 3.60 g (8.60 mmole) was combined with 1.29 g (8.60 mmole) trifluoromethane sulfonic acid and approximately 100 mL of 1,2-dichloroethane in a 200 mL round-bottomed flask equipped with a magnetic stirrer and nitrogen bubbler. The reaction mixture was allowed to stir for 24 hours at room temperature. The reaction solution was washed three times with 100 mL of saturated potassium carbonate solution and dried over sodium sulfate. The solvent was removed in vacuo and chromatographed on silica gel (30% ethyl acetate/70% hexane) to yield 0.40 g (11% of product).

EXAMPLE 4

Preparation of 2-(3-Cyano)phenylimino-3-(3-trifluoromethyl)phenyl-5-ethylthiazolidine A quantity of N-crotyl-N-(3-trifluoromethyl)phenyl-N'-(3-cyano)-phenylthiourea was prepared in accordance with the general procedures set forth in Examples 1 and 2, except that 3-cyanophenylisothiocyanate was used instead of 4-chloro-2-methylphenylisothiocyanate.

After the thiourea was prepared, 7.25 g (19.3 mmole) of the material was combined with 2.90 g (19.3 mmole) of trifluoromethane sulfonic acid and approximately 100 mL of 1,2-dichloroethane in a flask equipped with a magnetic stirrer and a nitrogen bubbler. The reaction mixture was allowed to stir under the nitrogen atmosphere at room temperature for 240 hours. The solution was washed three times with 100 mL of saturated potassium carbonate solution, and dried over sodium sulfate. The solvent was removed in vacuo and the residual oil chromatographed on silica gel (20% ethyl acetate/80% hexanes) to yield 2.56 g (36%) of product, which was identified by suitable analytical techniques.

EXAMPLE 5

Preparation of 2-Phenylimino-3-(3-trifluoromethyl)phenyl-5-ethyl-thiazolidine 2.10 g (5.99 mmole) of N-crotyl-N-(3-trifluoromethyl)phenyl-N'-phenylthiourea, prepared in accordance with the general procedures set forth in Examples 1 and 2, except that phenyl isothiocyanate was used instead of 4-chloro-2-methylphenylisothiocyanate, combined with 0.90 g (5.99 mmole) of trifluoromethane sulfonic acid and approximately 100 mL of 1,2-dichloroethane. The reaction solution was combined in a 250 mL round-bottomed flask equipped with a magnetic stirrer and nitrogen bubbler. The reaction solution was allowed to stir under nitrogen for 24 hours. The solution was washed three times with 50 mL of saturated potassium carbonate solution and dried over sodium sulfate. The solvent was removed in vacuo and the residual oil was chromatographed on silica gel (36% ethyl acetate/70% hexanes) to yield 1.45 g (69%) of product, which was identified by suitable analytical techniques.

Similar techniques can be used to prepare any of the other compounds produced in accordance with the process of this invention, simply varying the starting compounds and intermediate compounds.

The same general techniques were used to make the compounds set forth in Table I below.

TABLE I

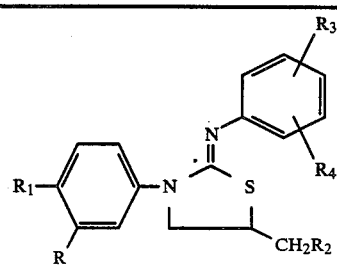

| Cmpd. No. | R | $R_1$ | $R_2$ | $R_3$ | $R_4$ |
|---|---|---|---|---|---|
| 1 | m-$CF_3$ | H | $CH_2CH_3$ | o-$CH_3$ | p-Cl |
| 2 | m-Cl | H | $CH_2CH_3$ | p-Cl | H |
| 3 | m-Cl | H | $CH_2CH_3$ | p-CN | H |
| 4 | m-Cl | H | $CH_2CH_3$ | m-Br | H |
| 5 | m-Cl | H | $CH_2CH_3$ | m-$CF_3$ | p-Cl |
| 6 | m-Cl | H | $CH_2CH_3$ | m-Cl | p-Cl |
| 7 | m-Cl | H | $CH_2CH_3$ | p-Cl | H |
| 8 | m-CN | H | $CH_2CH_3$ | m-Cl | H |
| 9 | m-$CF_3$ | H | $CH_2CH_3$ | p-CN | H |
| 10 | m-$CF_3$ | H | $CH_2CH_3$ | p-Cl | H |
| 11 | m-$CF_3$ | H | $CH_2CH_3$ | m-F | H |
| 12 | m-$CF_3$ | H | $CH_2CH_3$ | p-F | H |
| 13 | m-$CF_3$ | H | $CH_2CH_3$ | m-Cl | H |
| 14 | m-$CF_3$ | H | $CH_2CH_3$ | H | H |
| 15 | m-$CF_3$ | H | $CH_2CH_3$ | m-$CF_3$ | H |
| 16 | m-$CF_3$ | H | $CH_2CH_3$ | p-$CF_3$ | H |
| 17 | m-$CF_3$ | H | $CH_2CH_3$ | m-CN | H |
| 18 | m-$CF_3$ | H | $CH_2CH_3$ | m-Br | H |
| 19 | m-$CF_3$ | H | $CH_2CH_3$ | m-Cl | p-Cl |
| 20 | m-$CF_3$ | H | $CH_2CH_3$ | m-Cl | p-Cl |
| 21 | m-$CF_3$ | H | $CH_2CH_3$ | o-Cl | p-Cl |
| 22 | m-$CF_3$ | H | $CH_2CH_3$ | 3-Cl | 5-Cl |
| 23 | m-$CF_3$ | H | $CH_2CH_3$ | m-$CF_3$ | p-Cl |

What is claimed is:

1. A process for the preparation of iminothiazolidines compounds which comprises:

(a) reacting an N-3-substituted allyl aniline having the formula

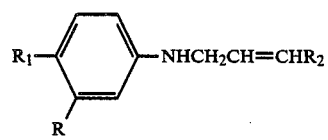

in which

R is halo, nitro, cyano, $C_1$–$C_4$ alkyl, $C_1$–$C_4$ alkoxy, pentahalomethyl, difluoromethyl, pentafluoroethyl, trifluoromethylthio, difluoromethoxy, trifluoromethoxy, tetrafluoroethoxy, methylsulfonyl, $C_1$–$C_4$ alkyloxyiminomethyl, benzyloxyiminomethyl, 1-($C_1$–$C_4$ alkyl)oxyiminoethyl or 1-benzyloxyiminoethyl;

$R_1$ is hydrogen or halo; and $R_2$ is $C_1$–$C_4$ alkyl or $C_1$–$C_4$ haloalkyl; with an arylisothiocyanate of the formula

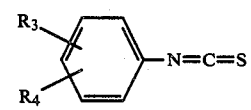

wherein $R_3$ and $R_4$ are independently hydrogen, halo, nitro, cyano, $C_1$–$C_4$ alkyl, $C_1$–$C_4$ haloalkyl, $C_1$–$C_4$ alkoxy, $C_1$–$C_4$ fluoroalkoxy or $C_1$–$C_4$ alkylthio, in the presence of an organic solvent and a suitable catalyst, at a temperature and for a sufficient period of time to yield an N,N'-diaryl-N-3-substituted allyl thiourea of the formula

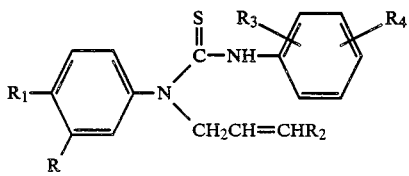

and (b) treating said N,N'-diaryl-N-3-substituted allyl thiourea with about one equivalent of methanesulfonic acid or trifluoromethanesulfonic acid in the presence of an aprotic solvent at a temperature of from about 20° C. to about 45° C. and for a sufficient period of time to produce an iminothiazolidine of the formula

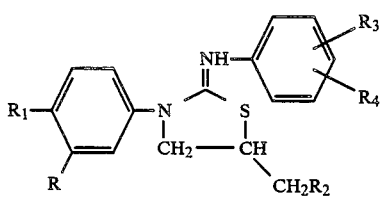

2. A process according to claim 1 in which R is halo, cyano, trifluoromethyl or trifluoromethylthio.

3. A process according to claim 1 conducted at atmospheric pressure.

4. A process according to claim 1 in which the aprotic solvent is a hydrocarbon or chlorinated hydrocarbon.

5. A process according to claim 1 in which the N-3-substituted aniline and the arylisothiocyanate are used in equimolar amounts.

6. A process for the preparation of iminothiazolidines which comprises reacting a thiourea of the formula

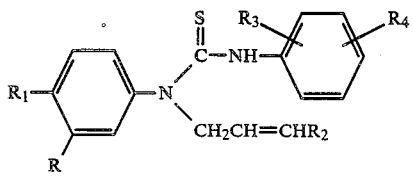

in which

R is halo, nitro, cyano, $C_1$–$C_4$ alkyl, $C_1$–$C_4$ alkoxy, pentahalomethyl, difluoromethyl, pentafluoroethyl, trifluoromethylthio, difluoromethoxy, trifluoromethoxy, tetrafluoroethoxy, methylsulfonyl, $C_1$–$C_4$ alkyloxyiminomethyl, benzyloxyiminomethyl, 1-($C_1$–$C_4$ alkyl)oxyiminoethyl or 1-benzyloxyiminoethyl;

$R_1$ is hydrogen or halo;

$R_2$ is $C_1$–$C_4$ alkyl or $C_1$–$C_4$ haloalkyl; and $R_3$ and $R_4$ are independently hydrogen, halo, nitro, cyano, $C_1$–$C_4$ alkyl, $C_1$–$C_4$ haloalkyl, $C_1$–$C_4$ alkoxy, $C_1$–$C_4$ fluoroalkoxy or $C_1$–$C_4$ alkylthio, with methanesulfonic acid or trifluoromethanesulfonic acid in the presence of an aprotic solvent at a temperature of from about 20° C. to about 45° C. and for a period of time sufficient to achieve cyclization of said thiourea to form said iminothiazolidine.

7. A process according to claim 6 in which R is halo, cyano, trifluoromethyl or trifluoromethylthio.

8. A process according the claim 6 conducted at atmospheric pressure.

9. A process according to claim 6 in which the aprotic solvent is a hydrocarbon or chlorinated hydrocarbon.

10. The process according to claim 6 in which the solvent is 1,2-dichloroethane.

* * * * *